(12) United States Patent
Spaulding et al.

(10) Patent No.: US 9,719,454 B2
(45) Date of Patent: Aug. 1, 2017

(54) HUMAN MACHINE INTERFACE (HMI) GUIDED MECHANICAL FUEL SYSTEM ADJUSTMENT

(71) Applicant: General Electric Company, Schenectady, NY (US)

(72) Inventors: Dennis John Spaulding, Waukesha, WI (US); Nathan Patrick Schaefer, Waukesha, WI (US); Robert Jarvis Selberg, Waukesha, WI (US); Derek Christopher Sammons, West Bend, WI (US)

(73) Assignee: General Electric Company, Schenectady, NY (US)

( * ) Notice: Subject to any disclaimer, the term of this patent is extended or adjusted under 35 U.S.C. 154(b) by 106 days.

(21) Appl. No.: 14/539,539

(22) Filed: Nov. 12, 2014

(65) Prior Publication Data
US 2016/0131070 A1     May 12, 2016

(51) Int. Cl.
| | | |
|---|---|---|
| *F02D 41/30* | (2006.01) | |
| *F02D 41/26* | (2006.01) | |
| *G01N 33/22* | (2006.01) | |
| *F02D 41/14* | (2006.01) | |
| *F02D 41/22* | (2006.01) | |

(52) U.S. Cl.
CPC ......... *F02D 41/3005* (2013.01); *F02D 41/26* (2013.01); *G01N 33/225* (2013.01); *F02D 41/1475* (2013.01); *F02D 2041/228* (2013.01)

(58) Field of Classification Search
CPC .. F02D 19/023; F02D 41/1498; G01M 13/00; G01M 15/00; G01M 15/10; G07C 5/004; Y02T 10/126; Y02T 10/40
USPC ......... 701/102–104, 114, 115; 123/295, 299, 123/300, 445, 677, 699, 700
See application file for complete search history.

(56) References Cited

U.S. PATENT DOCUMENTS

| | | | | |
|---|---|---|---|---|
| 4,393,842 A | * | 7/1983 | Otsuka | .................... F02D 41/28 123/445 |
| 4,765,305 A | * | 8/1988 | Hibino | ................ F02D 41/1489 123/684 |
| 5,574,645 A | | 11/1996 | Meeker et al. | |
| 5,742,276 A | | 4/1998 | Taraki | |
| 5,941,926 A | | 8/1999 | Taraki et al. | |
| 6,567,709 B1 | | 5/2003 | Malm et al. | |
| 6,631,310 B1 | | 10/2003 | Leslie | |

(Continued)

FOREIGN PATENT DOCUMENTS

| | | |
|---|---|---|
| AU | 2013101378 A4 | 11/2013 |
| CN | 1507536 A | 6/2004 |

(Continued)

*Primary Examiner* — John Kwon
*Assistant Examiner* — Johnny H Hoang
(74) *Attorney, Agent, or Firm* — Fletcher Yoder P.C.

(57) ABSTRACT

A display system for an engine includes a processor configured to receive a first measurement indication relating to a measurement of a fuel control valve position of the engine, wherein the fuel control valve position is configured to control an air/fuel ratio of the engine. The processor is further configured to compare the first measurement indication to a first preset fuel control valve range, generate a first completion indication based on when the measurement is within the first preset fuel control valve range, and display the first completion indication on a display of the display system.

20 Claims, 3 Drawing Sheets

(56) References Cited

U.S. PATENT DOCUMENTS

| | | |
|---|---|---|
| 7,040,286 B2 | 5/2006 | Campbell |
| 7,455,058 B2 | 11/2008 | Raffesberger |
| 2003/0236609 A1 | 12/2003 | Daniel et al. |
| 2008/0202469 A1* | 8/2008 | Kang ................... F02D 35/023 123/435 |
| 2010/0089364 A1* | 4/2010 | Flanagan ................ F02B 25/04 123/435 |
| 2012/0285228 A1 | 11/2012 | Grunbacher et al. |

FOREIGN PATENT DOCUMENTS

| | | |
|---|---|---|
| CN | 101634251 A | 1/2010 |
| CN | 102005999 A | 4/2011 |
| CN | 102953856 A | 3/2013 |
| EP | 2647821 A1 | 10/2013 |
| JP | 2009250051 A | 10/2009 |
| KR | 1048545 B1 | 7/2011 |
| RU | 2331048 C2 | 8/2008 |
| WO | 2007089741 A2 | 8/2007 |
| WO | 2013175404 A2 | 11/2013 |

\* cited by examiner

HUMAN MACHINE INTERFACE (HMI) GUIDED MECHANICAL FUEL SYSTEM ADJUSTMENT

BACKGROUND

The subject matter disclosed herein relates to fuel system adjustments on an engine, and, more specifically, to a control system with a display for adjusting a fuel control valve into specific positions.

An internal combustion engine is an engine where the combustion (i.e. burning) of a fuel occurs with an oxidizer (usually air) in a combustion chamber. In an internal combustion engine, the expansion of high-pressure gas produced by combustion applies a force to a piston, turbine, or other component of the engine. Thus, the internal combustion engine takes chemical energy from combustion and turns it into mechanical energy.

The ratio of fuel and air plays an important role in how the internal combustion engine functions. The air/fuel ratio to combust petrol may be, for instance, roughly 14.7:1, depending on the type and quality of fuel. A rich-burn engine may operate at an air/fuel ratio near that combustion point, such as near 16:1. In contrast, in a lean-burn engine, the engine burns fuel with an excess of air in the internal combustion engine, such as 65:1.

Rich burn engines have the benefits of being relatively simple, reliable, stable, and adapt well to changing loads. A rich burn engine may include a fuel control valve, such as a butterfly valve, that may be used to regulate the flow of air and/or fuel, thereby controlling emissions. Rich burn engines may include a regulator and/or a carburetor. The regulator and/or carburetor may include screws or other controls for setting the butterfly valve into a correct position. Currently, the regulator and/or carburetor adjustments are made at initial commissioning. Additionally, an operator may inappropriately change these adjustments in attempts to fix other problems. In such cases, the adjustments must be reset by a qualified technician to ensure good emissions control performance. However, these adjustments are currently guided by paper manuals and manometer readings which may be difficult to successfully calibrate to the desired operating positions. Moreover, many measurements must be taken, wasting time and resources. Accordingly, a need exists for an improved system of adjusting the fuel control valve to its desired position.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a display system for an engine includes a processor configured to receive a first measurement indication relating to a measurement of a fuel control valve position of an engine, wherein the fuel control valve position is configured to control an air/fuel ratio of the engine, compare the first measurement indication to a first preset fuel control valve range, generate a first completion indication based on when the measurement is within the first preset fuel control valve range, and display the first completion indication on a display of the display system.

In a second embodiment, a non-transitory computer-readable medium having computer executable code stored thereon, the code includes instructions to receive a measurement indication relating to a measurement of a fuel control valve position of an engine, wherein the fuel control valve position is configured to control an air/fuel ratio of the engine, compare the measurement indication to a preset fuel control valve range, generate a completion indication based on when the measurement indication is within the preset fuel control valve range, and transmit a signal utilized to display the completion indication on a display.

In a third embodiment, a fuel system includes a fuel control valve configured to control an air/fuel ratio of an engine, a regulator including a regulator adjusting control configured to adjust the fuel control valve, a fuel flow restriction control configured to adjust the fuel control valve; and a display system, including a processor configured to receive a measurement indication relating to a measurement of a fuel control valve position of an engine, wherein the fuel control valve position is configured to control an air/fuel ratio of the engine, compare the measurement indication to a preset fuel control valve range, generate a completion indication based on when the measurement is within the preset fuel control valve range, and display the completion indication on a display of the display system.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Figure 1:
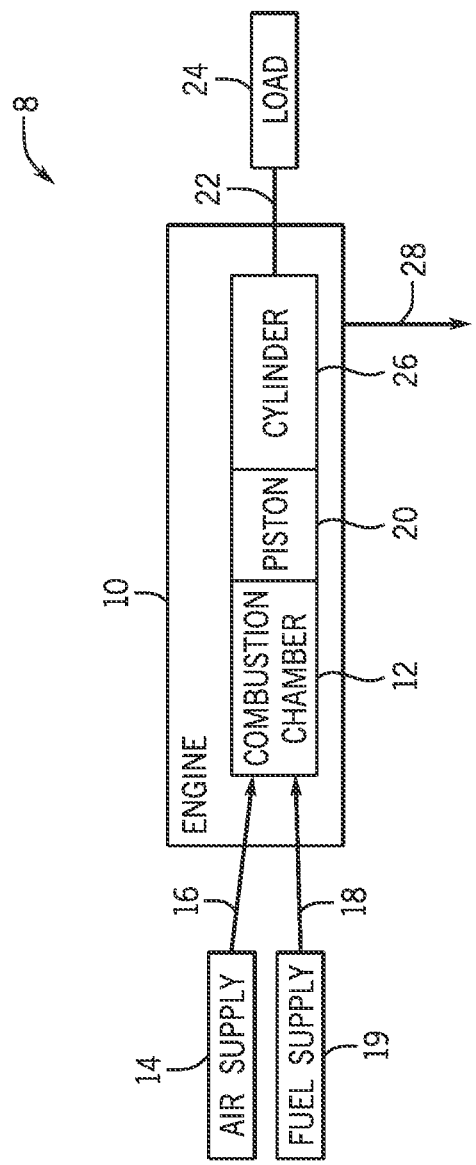
FIG. 1 is a block diagram of an embodiment of an engine system.

With the foregoing in mind, FIG. 1 illustrates a block diagram of a fuel adjustment system 8 for a rich burn engine.

While a rich burn engine is used as an example of how the fuel adjustment system 8 may be applied, the present disclosure may be used in any situation where an HMI guided fuel adjustment system 8 is desirable, such as rich, lean, reciprocating engine, turbine, or any combination thereof. For instance, the HMI guided fuel adjustment system 8 could be applied to a lean burn engine or a variety of turbines. The system 8 includes an engine 10 (e.g., a rich-burn engine) having one or more combustion chambers 12 (e.g., 1, 2, 3, 4, 5, 6, 7, 8, 10, 12, 14, 16, 18, 20, or more combustion chambers). An air supply 14 is configured to provide a pressurized oxidant 16, such as air, oxygen, oxygen-enriched air, oxygen-reduced air (including, but not limited to, exhaust gas recirculation), or any combination thereof, to each combustion chamber 12. The combustion chamber is also configured to receive a fuel 18 (e.g., a liquid and/or gaseous fuel) from a fuel supply 19, and an air-fuel mixture ignites and combusts within each combustion chamber 12. The hot pressurized combustion gases cause a piston 20 adjacent to each combustion chamber 12 to move linearly within a cylinder 26 and convert pressure exerted by the gases into a rotating motion, which causes a shaft 22 to rotate. The shaft 22 may be coupled to a load 24, which is powered via rotation of the shaft 22. For example, the load 24 may be any suitable device that may generate power via the rotational output of the system 10, such as an electrical generator.

Once the available energy is translated into rotating the shaft 22, the remaining fuel 18 and/or oxidant 16 is vented and removed from the engine 10 as exhaust 28. Although the following discussion refers to air as the oxidant 16, any suitable oxidant may be used with the disclosed embodiments. Similarly, the fuel 18 may be any suitable gaseous fuel, such as natural gas, associated petroleum gas, propane, biogas, sewage gas, landfill gas, coal mine gas, for example. Moreover, in some instances, the fuel 18 may vary in quality depending on the type and the environment the fuel 18 originated from. Accordingly, the exhaust 28 may be based on the fuel 18 quality and the system 8 configuration.

Figure 2:
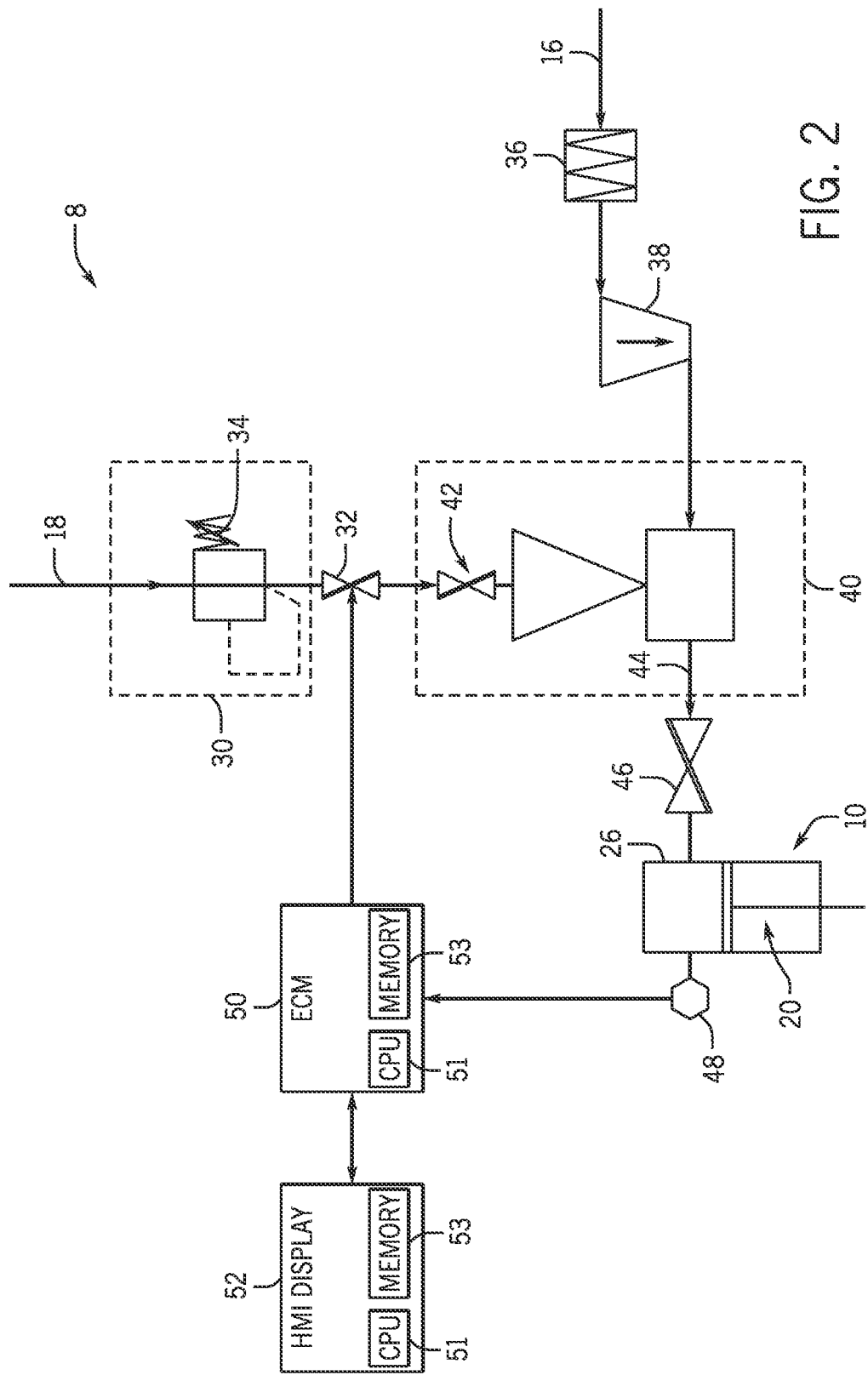
FIG. 2 is a schematic flow diagram of an exemplary engine system in accordance with the present techniques.

FIG. 2 is a schematic flow diagram of an exemplary fuel adjustment system 8 configuration in accordance with the present techniques. The fuel 18 may enter a regulator 30. The regulator 30 may regulate the fuel pressure to maintain a constant outlet pressure regardless of inlet pressure fluctuations. As such, the regulator 30 may control the flow of fuel by using a fuel control valve 32 (e.g., butterfly fuel valve) or fuel control actuator. Accordingly, an operator may adjust a regulator adjusting control (e.g., regulator adjusting screw) 34 of the regulator 30 to adjust the fuel control valve 32. While the regulator 30 uses an adjusting control 34 in an embodiment, this is merely an example. Alternatively, the regulator 30 may include a regulator adjusting screw, pilot adjusting screw, valve, or any adjustment system for adjusting the position of the fuel control valve 32.

The oxidant 16 (e.g., air) may enter a cleaner 36 to clean the oxidant 16. The clean oxidant 16 may then enter a turbo compressor 38 to compress the oxidant 16. While a cleaner 36 and a turbo compressor 38 are shown in FIG. 2, any additional and/or alternative method of preparing the oxidant 16 may be used. The fuel 18 and the air enter a carburetor 40 which blends the fuel 18 and/or air into an air/fuel mixture 44. The carburetor 40 has a fuel flow restriction control (e.g., carburetor screw) 42 that may be used to adjust the fuel control valve 32. While the carburetor 30 uses a fuel flow restriction control 42 (e.g., integral screw) in an embodiment, this is merely an example. Alternatively, the carburetor 30 may include a carburetor screw of a carburetor, valve, or any adjustment system for adjusting the position of the fuel control valve 32. Additionally or alternatively, a separate control, screw, or valve (e.g., venture type restriction valve) may be associated with the system.

The air/fuel mixture 44 then passes to a throttle 46 configured to regulate the amount of air/fuel mixture 44. As the throttle 46 is opened, the air/fuel mixture 44 passes to the engine 10 to be combusted to drive the piston 20 in the cylinder 26.

After the air/fuel mixture 44 is combusted in the engine 10, an O2 sensor 48 monitors the exhaust to detect rich, lean, or target mixtures. The target mixture may be a range or value of an air/fuel ratio that is known to produce desirable results. If the air/fuel mixture 44 has less air than the target mixture, fuel will be left over after combustion. This may be referred to as a rich mixture. Rich mixtures may cause additional undesirable emissions. Alternatively, a lean mixture may have more air and less fuel than the target mixture. A lean mixture may result in poor performance in addition to undesirable emissions. The O2 sensor 48 may detect a rich, lean, or target mixture based on, for instance, a chemical reaction that generates a voltage based on the mixture. The O2 sensor 48 may be configured to send signals to an electronic control module 50 (ECM). The ECM 50 may include a wide variety of inputs and outputs for controlling and/or monitoring a variety of sensors and/or actuators, including the O2 sensor 48 and the fuel control valve 32. The ECM 50 may communicate with a human-machine interface (HMI) display 52.

The ECM 50 and/or HMI display 52 may include a processor 51 or multiple processors 51, memory 53, and inputs/outputs. The processor 51 may be operatively coupled to the memory 53 to execute instructions for carrying out the presently disclosed techniques. These instructions may be encoded in programs or stored in a tangible non-transitory computer-readable medium, such as the memory 53 and/or other storage. The processor 51 may be a general purpose processor 51, system-on-chip (SoC) device, or application-specific integrated circuit, or some other processor 51 configuration. The memory 53 of the ECM 50 and/or HMI display 52, in an embodiment, includes a computer readable medium, such as, without limitation, a hard disk drive, a solid state drive, a diskette, a flash drive, a compact disk, a digital video disc, random access memory 53 (RAM), and/or any suitable storage device that enables the processor 51 to store, retrieve, and/or execute instructions and/or data. Memory 53 may include one or more local and/or remote storage devices.

The HMI display 52 may be an external display, locally or remotely, to display information to an operator. Alternatively, the HMI display 52 may be an internal display on the ECM 50. The HMI display 52 may be a panel that is located at the engine 10, or it may be located at a workstation. The HMI display 52 may be included with the system 8, or it may be a separate piece of hardware. The HMI display 52 may have connections, wireless or wired, to connect to the ECM 50 and/or other parts of the system 8. The display 52 may show information, such as charts, graphs, data, or instructions related to the ECM 50, the O2 sensor 48, the carburetor 40 and/or the fuel flow restriction control 42, the regulator 30 and/or the regulator adjusting control 34, the fuel control valve 32, or any other information related to the system 8.

As mentioned above, both the fuel flow restriction control 42 and the regulator adjusting control 34 control the fuel control valve 32, which controls the flow of fuel. Because the fuel flow restriction control 42 and the regulator adjusting control 34 impact the flow of fuel in different ways, it may be desirable to use both the fuel flow restriction control 42 and the regulator adjusting control 34 to ensure that the fuel control valve 32 has a desired operating authority (e.g., the fuel control valve position opens at a rate and an initial setting which provides target air/fuel mixtures at a variety of loads).

Figure 3:
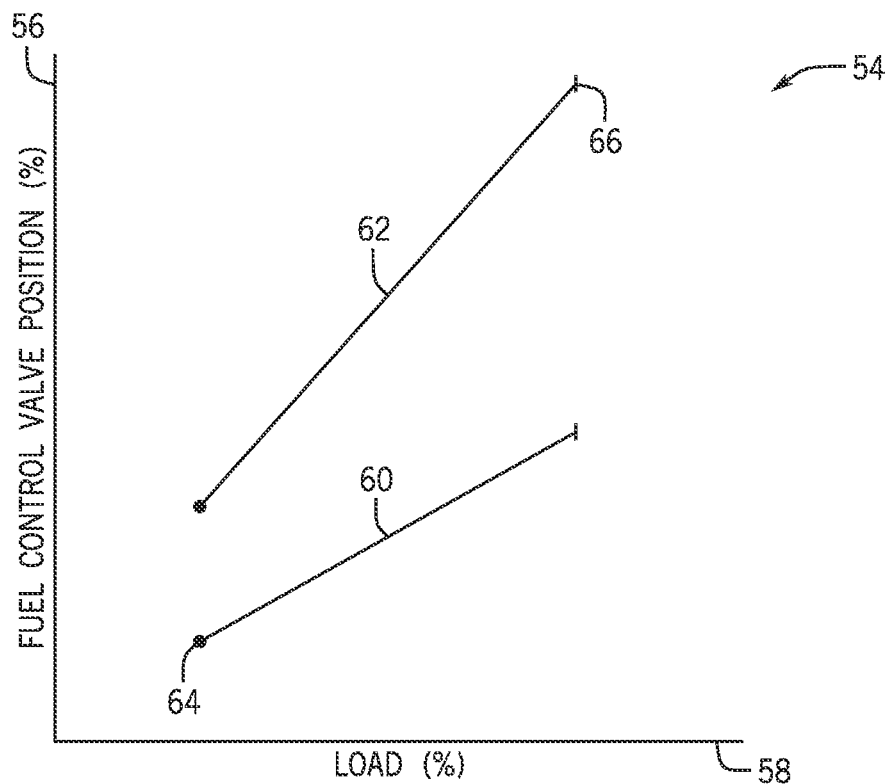
FIG. 3 is a graph illustrating an embodiment of the data received by the HMI display system of FIG. 2.

FIG. 3 is a graph 54 illustrating an embodiment of the data received by the ECM 50 of FIG. 2. The graph 54 shows the fuel control valve 32 position, such as a butterfly fuel valve position, as a percentage (e.g., percentage open) on the Y axis 56. The X axis 58 of the graph 54 shows the percentage load. The graph 54 includes a first line 60 and a second line 62. The first line 60 represents the fuel valve 32 position and percentage load at a low speed (e.g., 800 rpm). The first line 60 and second line 62 may start at a low percentage load (e.g., 10% or a value less than 50%) and run all the way to a high percentage load (e.g., 100% or a value greater than 50%). At a low load and/or low speed (e.g., rpm), such as point 64, the regulator adjusting control 34 may be used to set the fuel control valve 32 position to, for instance, 20-35%. The second line 62 represents the fuel valve 32 position and percentage load at a high speed (e.g., 1200 rpm). At a high load and a high speed (e.g., rpm), such as point 66, the fuel control valve 32 may be set to 45-60% with the fuel flow restriction control 42. While low and high rpm values are suggested above, they are merely for illustrative purposes to show the desired operating authority of the fuel control valve 32 with different loads and speeds. In an embodiment, the fuel flow restriction control 42 associated with the carburetor 40 may have less impact than the regulator adjustment control 34 on the fuel control valve 32 position at low load and/or speed. Thus, the operator may adjust the regulator adjusting control 34 at low load and low speed, thereby setting the Y intercept of the graph 54. Once the operator sets the Y intercept of the graph, the slope can be set with the fuel flow restriction control 42 at high load and high speed. Furthermore, while example values are given with a 1200 rpm engine 10 above, the numbers are merely for illustrative purposes, and the system disclosed herein may be used with a variety of fuel valve position values, loads, speeds, regulators, carburetors, and engines where an HMI display is desired.

Figure 4:
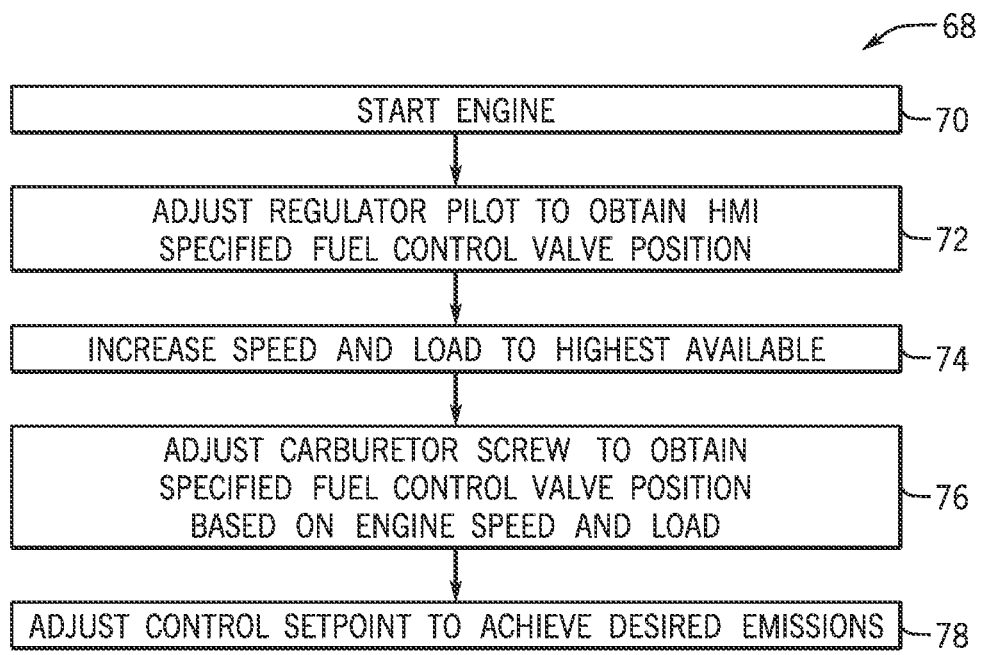
FIG. 4 is a flow diagram of an exemplary method in accordance with the present techniques.

As explained above, the regulator adjusting control 34 and the fuel flow restriction control 42 are adjusted to track the fuel control valve 32 position to the desired operating authority. FIG. 4 is a flow diagram 68 of an exemplary method in accordance with the present techniques to adjust the fuel control valve 32 position. The display 52 may first instruct the operator to set the fuel flow restriction control 42 and/or the regulator adjusting control 34 to an initial setting. For instance, the HMI display 52 may instruct the operator to rotate the fuel flow restriction control 42 4-6 full turns from the fully closed position and set the regulator control 34 1-1.5 in. out from a regulator cap. Once the system 8 is set in an initial setting, the engine 10 is started. Then, the display 52 may show instructions to the operator for setting the needed speed and load. Initially, the instructions may request that the engine 10 be set at a low speed and low load.

The HMI display 52 and/or the ECM 50 may receive engine 10 signals related to measurements of the engine speed, load, or any combination thereof. Once the operator sets the speed and load settings within a speed range and/or a load range, the display 52 may provide a first load indication that the settings are within the correct range, or that the speed and/or load is currently operating within the correct range. The first load indication may be a message on the display 52 stating the current speed and/or load, or it may simply display a message stating that the speed and load settings and/or current operation is within the speed range and load range. If the measurements of the speed and/or load received by the display 52 and/or ECM 50 are above a maximum value, the display 52 may provide a warning indication configured to warn the operator that the speed and/or load is too high for adjusting the regulator adjusting control 34. The operator may then adjust (block 72) the regulator adjusting control 34 until the fuel control valve 32 is within a preset fuel control valve range. The preset fuel control valve range could be a target value with a margin of error (e.g., 27+/−3%), or the range may include a minimum and maximum (24-30%). While the operator is adjusting the regulator adjusting control 34, the ECM may receive signals related to measurements from the fuel control valve 32.

The display 52 and/or the ECM 50 may include computer executable code. The code may include instructions to receive a first measurement indication relating to a measurement of the fuel control valve 32 position of the engine 10. The first measurement indication may correspond to a percentage that the fuel control valve 32 is open/closed. The display 52 and/or the ECM 50 may then compare the first measurement indication to a preset fuel control valve 32 range. The preset fuel control valve 32 range may correspond to a desired air/fuel ratio range at the low load and/or speed which is known to provide a target mixture. The first measurement indication may include an adjustment configured to instruct the user how to adjust the regulator adjustment control 34. The adjustment may indicate a direction (e.g., in, out, clockwise, counterclockwise) and/or a quantity (e.g., number of rotations or degrees). As the operator adjusts the regulator adjusting control 34, it sets point 64 on FIG. 3, thereby adjusting the Y-intercept of the graph 54.

The display 52 and/or the ECM 50 may generate a first completion indication based on when the first measurement indication is within the preset fuel control valve 32 range. The first completion indication may be proceeding to the next step, displaying a message saying that the step is complete, or it may be displaying the current fuel valve 32 position within the preset fuel control range. The first completion indication and/or the first measurement indication may be displayed on the display 52.

Once the regulator adjusting control 34 has been adjusted to the desired setting, the display 52 may instruct the operator to increase (block 74) the engine speed and load to a maximum available. The maximum available speed and load may be the operational maximum of the engine (e.g., how fast the machine was designed to go). Alternatively, it may be below the operational maximum (e.g., less than 100% load) but above a minimum value (e.g., above 50% load, 90% load, 98% load, or above the first load indication). The minimum value may be a preset value that corresponds to a desired operating authority for the butterfly fuel valve. If the measurements of the speed and/or load received by the display 52 and/or ECM 50 are below the minimum value, the display 52 may provide a warning indication configured to warn the operator that the speed and/or load is too low for adjusting the fuel flow restriction control 42. Once the minimum value has been reached and/or the settings have been set, the display 52 may provide a second load indication configured to provide the operator with an indication that the speed and load are above the minimum values and/or set to exceed the minimum values. The second load indication may be advising the operator to proceed to the next step, displaying the current speed and/or load above the minimum values, displaying a message stating that the current speed and/or load are above the minimum values, or simply displaying the next step on the display 52.

Once the second load indication is provided to the operator, the operator may then adjust the fuel flow restriction control 42 to obtain a specified fuel control valve 32 position based on the engine speed and the load (block 76). The specified fuel control valve 32 position may be a fuel control valve 32 range or it may be a target value with a margin of error (e.g., 45 plus/minus 3%). Similar to the regulator screw procedure, the HMI display 52 may display the current left and/or right fuel valve position.

Similar to the regulator screw procedure (block 72) above, the display 52 may include code with instructions to receive a second measurement indication relating to a measurement of the fuel control valve 32 position of the engine 10. The second measurement indication may correspond to a percentage that the fuel control valve 32 is open/closed. The display 52 and/or the ECM 50 may then compare the second measurement indication to the specified fuel control valve position based on the high engine speed and load. If the second measurement indication falls within the range or margin of error of the specified fuel control valve position, the fuel control valve 32 position may correspond to a desired air/fuel ratio range at high load and/or speed known to provide proper operating authority. The specified fuel control valve position may be preset based on known positions and ranges that are known to provide proper operating authority at different operating points on the graph 54. The second measurement indication may include an adjustment configured to instruct the user how to adjust the fuel flow restriction control 42. The adjustment may indicate a direction (e.g., in, out, clockwise, counterclockwise) and/or a quantity (e.g., number of rotations or degrees). As the operator adjusts the fuel flow restriction control 42, it adjusts point 66 on FIG. 3, thereby altering the slope of the graph 54 and creating a line 62 corresponding to the desired operating authority.

Once the operator adjusts the fuel flow restriction control 42 to fall within the specified fuel control valve 32 range or margin of error, a second completion indication may be provided to the operator indicating that fuel control valve 32 position is within the desired operating authority. The second completion indication may be proceeding to the next step, displaying a message saying that the step is complete, or it may be displaying the current fuel valve 32 position and the specified fuel control valve 32 position. The second completion indication and/or the first measurement indication may be displayed on the display. In an embodiment, the HMI display 52 may also change the fuel control valve target/range based on the maximum available speed and load to allow flexibility in different situations.

The HMI display 52 and/or ECM 50 may include an emissions analyzer. The emissions analyzer may be in either hardware or software. As such, the emissions analyzer may include a memory communicatively coupled to a processor separate from the ECM 50 or HMI display 52, or the emissions analyzer may include computer executable code stored in the memory of the ECM 50 or HMI display 52. The code may include instructions to adjust a control setpoint for emissions. Using the emissions analyzer, the operator may adjust the control setpoint to achieve the desired emissions (block 78). As mentioned above, the emissions analyzer may communicate with the O2 sensor, which can detect a rich, lean, or target mixture based on a chemical reaction that generates a voltage based on the mixture. The control setpoint may correspond to a desired measurement of a voltage of the O2 sensor. A lean mixture tends to produce more nitrogen-oxide pollutants (e.g., NOx), while a rich mixture tends to produce more CO. Thus, if the NOx reading is high in the system 8, the operator may adjust the setpoint to rich. If the CO reading is high, then the operator may adjust the setpoint to lean. The emissions analyzer may include a pre-catalyst (e.g., setpoint 2V to 2.003V) and/or post catalyst mode (e.g., setpoint 0.680V to 0.750V). The emissions analyzer may display an exhaust measurement indication on the display. The exhaust measurement indication may correspond to the current measurement of the O2 sensor.

Technical effects of the present embodiments relate to an HMI display 52 useful in controlling and adjusting the fuel control valve position and/or emissions of an engine. Specifically, the HMI display 52 may generate signals related to positioning the regulator adjusting control 34 and the fuel flow restriction control 42, which corresponds to the fuel control valve 32 position. The HMI display 52 may generate measurement indications related to the percentage that the fuel control valve 32 is open/closed or left/right. The HMI display 52 may generate adjustment indications indicating which way to turn the regulator adjusting control 34 and/or the fuel flow restriction control 42. In certain embodiments, the HMI display 52 may generate completion indications when steps are complete. Additionally, the HMI display 52 may adjust a control setpoint for emissions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A display system for an engine, comprising a processor configured to:
    receive a first data measurement indicative of a position of a fuel control valve that controls an air/fuel ratio of the engine;
    compare the first data measurement to a first fuel control valve range, wherein the first fuel control valve range corresponds to a target air/fuel ratio while the engine operates at a low engine speed, a low engine load, or both;
    generate an indication of an adjustment to be made via a regulator based on the position of the fuel control valve and the first fuel control valve range;
    display a first completion indication related to completion of the adjustment made via the regulator;
    receive a second data measurement indicative of the position of the fuel control valve;
    compare the second data measurement to a second fuel control valve range, wherein the second fuel control valve range corresponds to a target air/fuel ratio while the engine is operating at a high engine speed higher than the low engine speed, a high engine load higher than the low engine load, or both;
    generate an indication of an adjustment to be made to a carburetor based on the position of the fuel control valve and the second fuel control valve range; and display a second completion indication related to completion of the adjustment made via the carburetor on the display.

2. The display system of claim 1, wherein the processor of the display system is configured to:
  display the first fuel control valve range on the display; and
  display the first data measurement within the first fuel control valve range on the display as the first completion indication.

3. The display system of claim 1, wherein the processor is configured to display a target fuel valve position and a tolerance associated with the target fuel valve position as the first fuel control valve range.

4. The display system of claim 1, wherein the processor is configured to display an exhaust measurement indication from an oxygen sensor on the display, wherein the exhaust measurement indication corresponds to a measurement of the air/fuel ratio.

5. The display system of claim 1, wherein the first data measurement is displayed on the display before the second data measurement is displayed on the display.

6. The display system of claim 1, wherein the processor is configured to display an exhaust measurement indication and a control setpoint on the display, wherein the exhaust measurement indication is indicative of the air/fuel ratio of the engine, and wherein the control setpoint adjusts the air/fuel ratio by adjusting the position of the fuel control valve.

7. A non-transitory computer-readable medium having computer executable code stored thereon, the code comprising instructions to:
  receive a first data measurement indicative of a position of a fuel control valve that controls an air/fuel ratio of an engine;
  compare the first data measurement to a first fuel control valve range, wherein the first fuel control valve range corresponds to a target air/fuel ratio while the engine operates at a low engine speed, a low engine load, or both;
  generate an indication of an adjustment to be made via a regulator based on the position of the fuel control valve and the first fuel control valve range;
  transmit a signal to display a first completion indication related to completion of the adjustment via the regulator on a display;
  receive a second data measurement indicative of the position of the fuel control valve;
  compare the second data measurement to a second fuel control valve range, wherein the second fuel control valve range corresponds to a target air/fuel ratio while the engine is operating at a high engine speed higher than the low engine speed, a high engine load higher than the low engine load, or both;
  generate an indication of an adjustment to be made to a carburetor based on the position of the fuel control valve and the second fuel control valve range; and
  transmit a signal to display a second completion indication related to completion of the adjustment made via the carburetor on the display.

8. The non-transitory computer-readable medium of claim 7, wherein the first fuel control valve range and the second fuel control valve range are associated with an operating authority, wherein the operating authority comprises an initial value and a slope of the air/fuel ratio at one or more engine speeds, one or more engine loads, or both.

9. The non-transitory computer-readable medium of claim 7, wherein the instructions comprise instructions to provide an adjustment configured to instruct a user how to adjust a regulator adjustment control of the regulator.

10. The non-transitory computer-readable medium of claim 7, wherein the first fuel control valve range comprises a target fuel valve position and a tolerance associated with the target fuel valve position.

11. The non-transitory computer-readable medium of claim 7, comprising instructions to generate an exhaust measurement indication and a control setpoint, wherein the exhaust measurement indication is indicative of the air/fuel ratio of the engine, and wherein the control setpoint adjusts the air/fuel ratio by adjusting the position of the fuel control valve.

12. A fuel system, comprising:
  a fuel control valve configured to control an air/fuel ratio of an engine;
  a regulator comprising a regulator adjusting control configured to adjust the fuel control valve;
  a fuel flow restriction control configured to adjust the fuel control valve; and
  a display system, comprising a processor configured to:
    receive a first data measurement indicative of a position of the fuel control valve that controls an air/fuel ratio of the engine;
    compare the first data measurement indication to a first fuel control valve range, wherein the first fuel control valve range corresponds to a target air/fuel ratio while the engine operates at a low engine speed, a low engine load, or both;
    generate an indication of an adjustment to be made via the regulator adjusting control based on the position of the fuel control valve and the first fuel control valve range;
    display a first completion indication related to completion of the adjustment via the regulator adjusting control on a display of the display system;
    receive a second data measurement indicative of the position of the fuel control valve;
    compare the second data measurement to a second fuel control valve range, wherein the second fuel control valve range corresponds to a target air/fuel ratio while the engine is operating at a high engine speed higher than the low engine speed, a high engine load higher than the low engine load, or both;
    generate an indication of an adjustment to be made to the fuel flow restriction control based on the position of the fuel control valve and the second fuel control valve range; and
    display a second completion indication related to completion of the adjustment made via the carburetor on the display.

13. The fuel system of claim 12, wherein the processor is configured to display the data measurement of the position of the fuel control valve as a percentage, degree, step, inches, centimeters, duration, duty cycle, frequency, or any combination thereof as the first data measurement.

14. The fuel system of claim 12, wherein the first fuel control valve range and the second fuel control valve range are associated with an operating authority, wherein the operating authority comprises an initial value and a slope of the air/fuel ratio at one or more engine speeds, one or more engine loads, or both.

15. The fuel system of claim 12, wherein the system comprises an electronic control module connected to the display system, wherein the electronic control module is configured to control the position of the fuel control valve.

16. The fuel system of claim 12, wherein the processor is configured to display an exhaust measurement indicative of a control setpoint on the display, wherein the exhaust measurement is related to the air/fuel ratio of the engine, and wherein the control setpoint adjusts the air/fuel ratio by adjusting the position of the fuel control valve.

17. The fuel system of claim 12, wherein the first fuel control valve range comprises a target fuel valve position and a tolerance associated with the target fuel valve position.

18. The fuel system of claim 12, wherein the first completion indication comprises proceeding to a next step, displaying a message indicating that a step is complete, displaying the position of the fuel control valve and the first fuel control valve range, or any combination thereof.

19. The fuel system of claim 12, wherein the fuel flow restriction control comprises a carburetor screw.

20. The fuel system of claim 12, wherein the regulator adjusting control comprises a regulator adjusting screw.

* * * * *